US00PP19860P2

(12) United States Plant Patent
Lubbe

(10) Patent No.: US PP19,860 P2
(45) Date of Patent: Mar. 31, 2009

(54) ***SALVIA* PLANT NAMED 'BLUE LIPS'**

(50) Latin Name: *Salvia bulleyana*
Varietal Denomination: Blue Lips

(75) Inventor: Remy Lubbe, Noordwijkherhout (NL)

(73) Assignee: Molter B.V., Noordwijkherhout (NL)

( * ) Notice: Subject to any disclaimer, the term of this patent is extended or adjusted under 35 U.S.C. 154(b) by 0 days.

(21) Appl. No.: 12/074,420

(22) Filed: Mar. 3, 2008

(51) Int. Cl.
*A01H 5/00* (2006.01)

(52) U.S. Cl. ..... Plt./475
(58) Field of Classification Search ..... Plt./475
See application file for complete search history.

*Primary Examiner*—Kent L Bell
(74) *Attorney, Agent, or Firm*—C. A. Whealy

(57) ABSTRACT

A new and distinct cultivar of *Salvia* plant named 'Blue Lips', characterized by its upright plant habit; freely branching habit; freely flowering habit; and yellow and dark purple-colored flowers.

2 Drawing Sheets

Botanical designation: *Salvia bulleyana.*
Cultivar denomination: 'Blue Lips'.

BACKGROUND OF THE INVENTION

The present invention relates to a new and distinct cultivar of *Salvia,* botanically known as *Salvia bulleyana* and hereinafter referred to by the name 'Blue Lips'.

The new *Salvia* is a naturally-occurring whole plants mutation of an unnamed selection of *Salvia bulleyana,* not patented. The new *Salvia* was discovered and selected by the Inventor as a single flowering plant from within a population of plants of the unnamed selection in a controlled environment in Noordwijkerhout, The Netherlands in August, 2004.

Asexual reproduction of the new cultivar by vegetative cuttings in a greenhouse in Noordwijkerhout, The Netherlands, since 2005, has shown that the unique features of this new *Salvia* are stable and reproduced true to type in successive generations.

SUMMARY OF THE INVENTION

Plants of the cultivar Blue Lips have not been observed under all possible environmental conditions. The phenotype may vary somewhat with variations in environment such as temperature and light intensity without, however, any variance in genotype.

The following traits have been repeatedly observed and are determined to be the unique characteristics of 'Blue Lips'. These characteristics in combination distinguish 'Blue Lips' as a new and distinct cultivar:

1. Upright plant habit.
2. Freely branching habit.
3. Freely flowering habit.
4. Yellow and dark purple-colored flowers.

Plants of the new *Salvia* differ from plants of the parent selection primarily in flower color as plants of the parent selection have pale purple-colored flowers.

Plants of the new *Salvia* can be compared to plants of the cultivar Rhapsody in Blue, disclosed in U.S. Plant Pat. No. 15,148. In side-by-side comparisons conducted by the Inventor in Noordwijkerhout, The Netherlands, plants of the new *Salvia* differed from plants of the cultivar Rhapsody in Blue in the following characteristics:

1. Plants of the new *Salvia* were not as compact as plants of the cultivar Rhapsody in Blue.
2. Plants of the new *Salvia* were not as dense and bushy as plants of the cultivar Rhapsody in Blue.
3. Plants of the new *Salvia* and the cultivar Rhapsody in Blue differed in flower color as plants of the cultivar Rhapsody in Blue had purple-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Salvia.*

The photograph on the first sheet comprises a side perspective view of a typical flowering plant of 'Blue Lips' grown in an outdoor nursery.

The photograph on the second sheet is a close-up view of typical flowers of 'Blue Lips'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and following description were grown under conditions which closely approximate commercial production conditions during the late summer in an outdoor nursery in Noordwijkerhout, The Netherlands. During the production of the plants, day temperatures averaged 20° C. and night temperatures averaged 14° C. Plants were pinched one time about two weeks after planting. Plants used for the photographs and description were about two years old.

Botanical classification: *Salvia bulleyana* cultivar Blue Lips.
Parentage: Naturally-occurring whole plant mutation of an unnamed selection of *Salvia bulleyana,* not patented.

Propagation:

*Type cutting.*—Vegetative cuttings.

*Time to initiate roots, summer.*—About three weeks at 20° C.

*Time to initiate roots, winter.*—About four weeks at 12° C.

*Time to produce a rooted young plant, summer.*—About 50 days at 20° C.

*Time to produce a rooted young plant, winter.*—About 70 days at 12° C.

*Root description.*—Fine, freely branching; color, 177A.

Plant description:

*Form.*—Herbaceous perennial. Upright plant form. Freely basal branching with about five main stems; vigorous growth habit. Flowers arranged in verticillasters on spikes.

*Plant height.*—About 60 cm.

*Plant width.*—About 40 cm.

*Lateral branch description.*—Length: About 40 cm. Diameter: About 6 mm. Internode length: About 14 cm. Strength: Strong. Aspect: Mostly upright. Texture: Smooth, glabrous. Color: Close to 144A.

Foliage description:

*Arrangement.*—Opposite, simple.

*Length.*—About 20 cm.

*Width.*—About 8 cm.

*Shape.*—Deltoid.

*Apex.*—Acute.

*Base.*—Sagittate.

*Margin.*—Crenate.

*Texture, upper and lower surfaces.*—Setaceous, rough.

*Venation pattern.*—Pinnate.

*Color.*—Developing foliage, upper surface: Close to 143A. Developing foliage, lower surface: Close to 139C. Fully expanded foliage, upper surface: Close to 137A; venation, close to 142C. Fully expanded foliage, lower surface: Close to 138B; venation, close to 142C.

*Petiole length.*—About 12 cm.

*Petiole diameter.*—About 7 mm.

*Petiole texture, upper and lower surfaces.*—Setaceous, rough.

*Petiole color, upper surface.*—139B, towards the base, N79B.

*Petiole color, upper surface.*—138A, towards the base, N79B.

Flower description:

*Flower arrangement and shape.*—Single bilabiate flowers arranged in verticillasters on spikes; flowers drooping. Freely flowering habit, about 90 to 110 flowers per inflorescence.

*Natural flowering season.*—Continuous flowering from late summer to early autumn in The Netherlands.

*Flower longevity on the plant.*—About two days; flowers not persistent.

*Flower buds.*—Length: About 2 mm to 12 mm. Diameter: About 2 mm to 5 mm. Shape: Oblong. Color: Close to 141C.

*Inflorescence size.*—Length: About 40 cm. Diameter: About 20 cm.

*Flowers.*—Diameter: About 8 mm to 10 mm. Depth (height): About 2 cm to 3 cm.

*Petals.*—Arrangement: Two, fused at the base. Length: About 2.5 cm. Width: About 1 cm. Shape, upper lip: Broadly elliptic; apex, hooked; base, acute; margin, entire. Shape, lower lip: Orbicular; apex, bi-lobed; base, acute; margin, entire. Texture, upper and lower surfaces: Pubescent. Color: Upper lip, when opening and fully opened, upper and lower surfaces: Close to 11A. Lower lip, when opening and fully opened, upper and lower surfaces: Close to 79B.

*Calyx.*—Shape: Three to five sepals fused into a tube. Length: About 1 cm. Width: About 6 mm. Texture, upper and lower surfaces: Pubescent. Color, upper surface: Close to 143A. Color, lower surface: Close to 143C.

*Pedicels.*—Strength: Strong. Length: About 6 mm. Diameter: About 2 mm. Aspect: About 45° from vertical. Texture: Pubescent. Color: Close to 144B.

*Reproductive organs.*—Stamens: Quantity per flower: Two. Filament length: About 5 mm to 10 mm. Filament color: Close to 155A. Anther shape: Ovate. Anther length: About 9 mm to 12 mm. Anther color: Close to N186A. Pollen amount: None observed. Pistils: Quantity per flower: One. Pistil length: About 2.5 cm. Stigma shape: Rounded. Stigma color: Close to N77D. Style length: About 2.5 cm. Style color: Close to 11D. Ovary color: Close to 11D.

*Seed/fruit.*—Seed and fruit production has not been observed.

Disease/pest resistance: Plants of the new *Salvia* have not been noted to be resistant to pathogens and pests common to *Salvia*.

Garden performance: Plants of the new *Salvia* have exhibited good tolerance to rain and wind and have been observed to tolerate temperatures from about −20° C. to about 40° C.

It is claimed:

1. A new and distinct *Salvia* plant named 'Blue Lips' as illustrated and described.

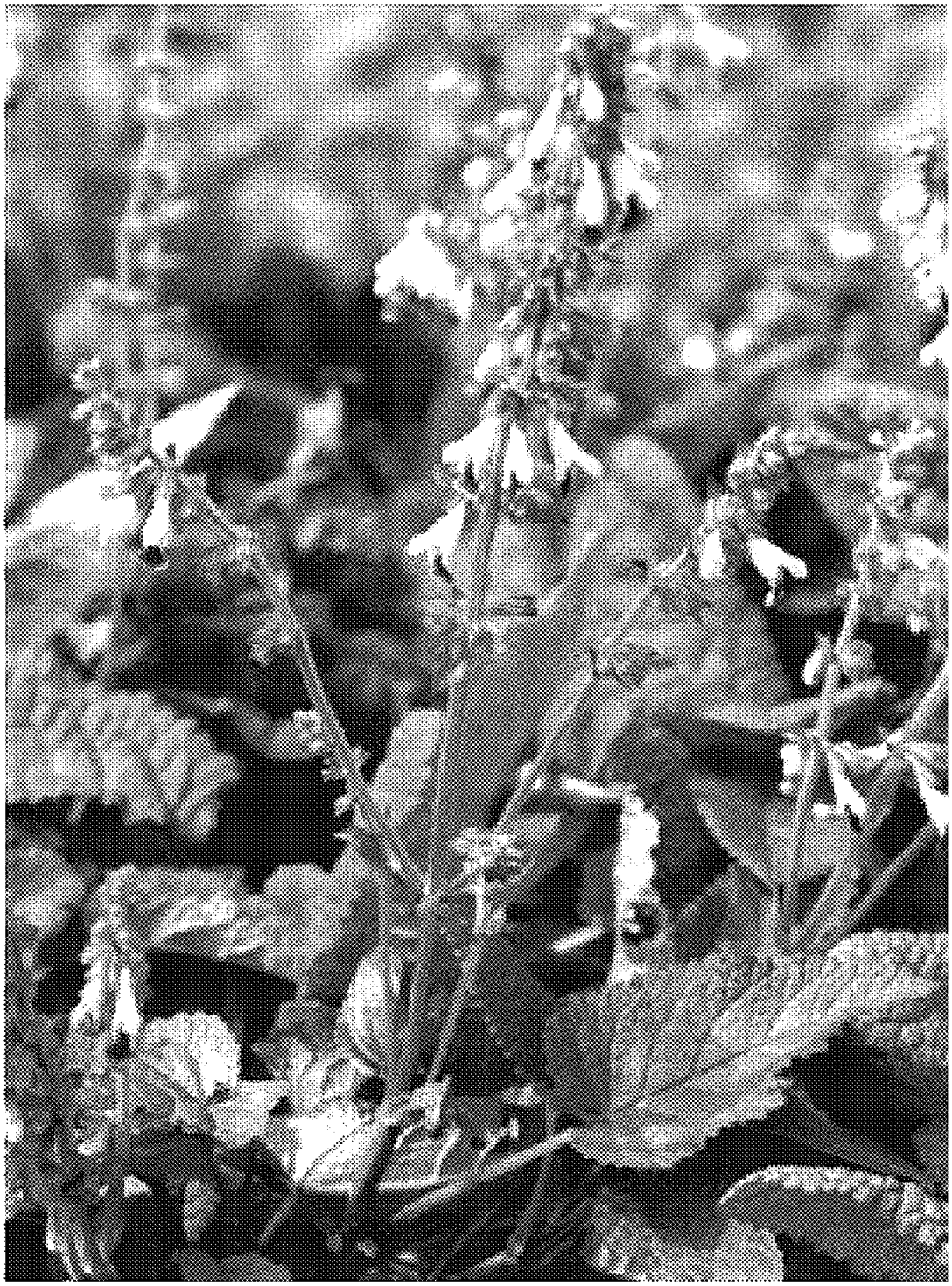

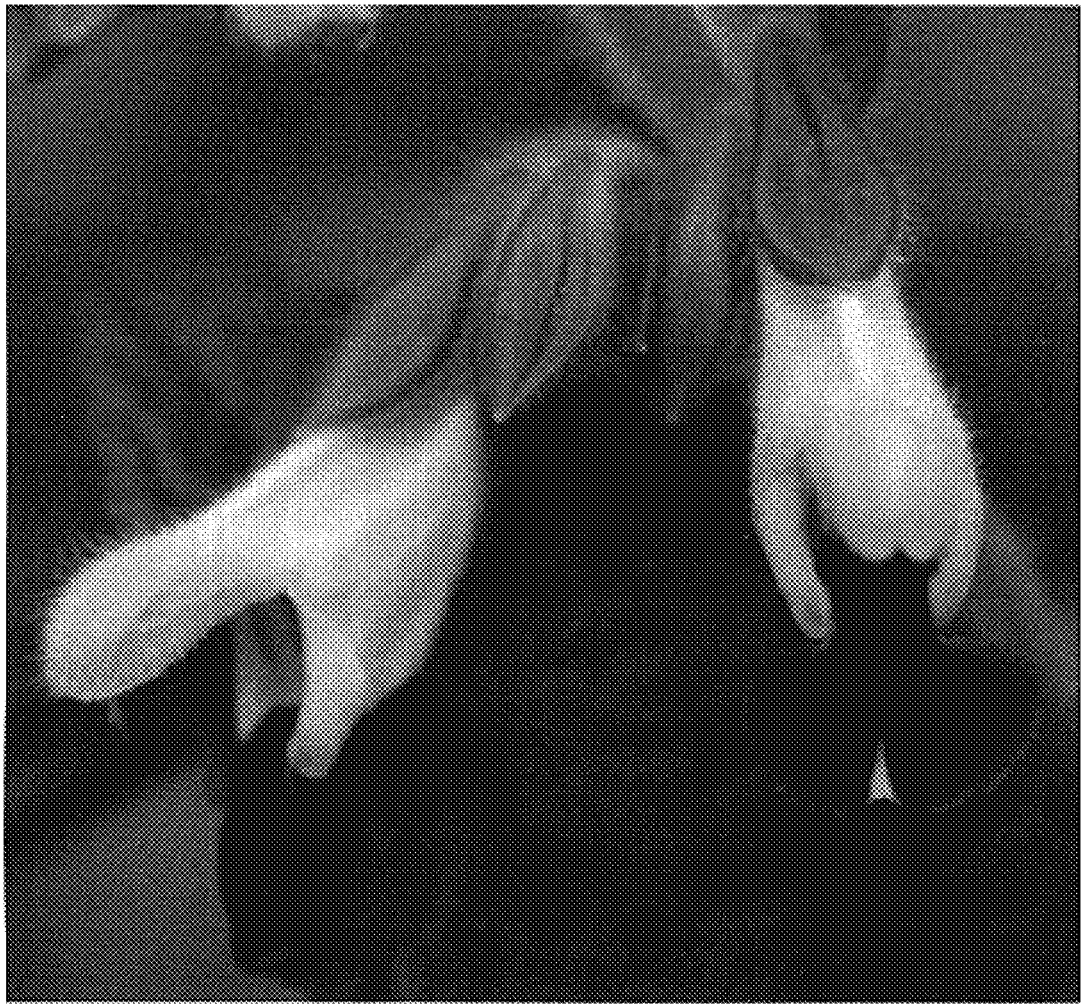

* * * * *